United States Patent
Eck et al.

(10) Patent No.: US 6,790,182 B2
(45) Date of Patent: Sep. 14, 2004

(54) ULTRASOUND SYSTEM AND ULTRASOUND DIAGNOSTIC APPARATUS FOR IMAGING SCATTERERS IN A MEDIUM

(75) Inventors: Kai Eck, Aachen (DE); Georg Schmitz, Roetgen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/945,859

(22) Filed: Sep. 4, 2001

(65) Prior Publication Data

US 2002/0049381 A1 Apr. 25, 2002

(30) Foreign Application Priority Data

Sep. 5, 2000  (EP) ............................................. 00402445

(51) Int. Cl.$^7$ .............................................. A61B 8/02
(52) U.S. Cl. ...................... 600/447; 600/437; 600/443
(58) Field of Search ................................. 600/437–472

(56) References Cited

U.S. PATENT DOCUMENTS

| | | | | |
|---|---|---|---|---|
| 4,413,629 A | * | 11/1983 | Durley, III ................... 600/437 |
| 5,117,832 A | * | 6/1992 | Sanghvi et al. ............. 600/459 |
| 5,454,372 A | * | 10/1995 | Banjanin et al. ............ 600/443 |
| 5,522,393 A | * | 6/1996 | Phillips et al. .............. 600/455 |
| 5,762,066 A | * | 6/1998 | Law et al. ................... 600/439 |
| 5,961,463 A | * | 10/1999 | Rhyne et al. ................ 600/458 |
| 5,984,869 A | * | 11/1999 | Chiao et al. ................. 600/455 |
| 6,213,947 B1 | * | 4/2001 | Phillips ....................... 600/455 |

* cited by examiner

*Primary Examiner*—Marvin M. Lateef
*Assistant Examiner*—William Jung
(74) *Attorney, Agent, or Firm*—John Vodopia

(57) ABSTRACT

An ultrasound imaging system for imaging ultrasound scatterers, comprising a probe (208) for transmitting ultrasound waves and detecting ultrasound echoes reflected by said ultrasound scatterers, wherein said probe comprises a first group of transducer elements, labeled transmitting group (T), to transmit ultrasound waves, and a distinct second group of transducer elements, labeled receiving group (R), to detect ultrasound echoes reflected by said ultrasound scatterers. The system also comprises a processing system (202) comprising transmission and reception means, coupled to said probe (208), for providing coded signal to said transmitting group (T) and receiving signals from said receiving group (R) respectively; transmission beam-forming means (103) for focussing the ultrasound waves on a focus line, reception beam-forming means (105) for forming beam-summed received signals from signals received from the focus line and processing means for processing said beam-summed received signals to form decoded signals so as; and means for displaying an image (109) that is a function of said decoded signals.

10 Claims, 3 Drawing Sheets

ULTRASOUND SYSTEM AND ULTRASOUND DIAGNOSTIC APPARATUS FOR IMAGING SCATTERERS IN A MEDIUM

FIELD OF THE INVENTION

The invention relates to an ultrasound system associated with a probe for imaging ultrasound scatterers in a medium. The invention also relates to an ultrasound diagnostic imaging apparatus, including such a system and a probe, for increasing the signal-to-noise ratio (SNR) in medical ultrasound imaging.

BACKGROUND OF THE INVENTION

A method and apparatus for improving the SNR in medical ultrasound imaging is described in the patent U.S. Pat. No. 5,984,869 (Chiao and alii). This document relates to a method and an apparatus that increase the signal-to-noise ratio (SNR) in medical ultrasound imaging by using Golay-coded excitation signals. A low SNR causes a limited penetration depth and a small dynamic range of the image, thus lowering the diagnostic information of the ultrasonic image. This document proposes a solution to obtain a good SNR, which consists in increasing the signal energy. By using coded signals (e.g. chirp signals, maximum sequences or Barker/Golay codes) the signal energy is increased by a factor of typically 10–80, depending on the length of the coded signals without increasing the maximum amplitude of the ultrasonic signal.

Coded signals present the characteristics to have a long duration compared to conventional pulse excitation signals. So, one significant problem is that the maximum duration of coded signals is limited by the propagation period of these coded signals, which is calculated as twice the distance between the probe and the area to be imaged divided by the propagation velocity of sound in tissue. Therefore, the use of coded signals with a duration longer than twice the propagation period of these coded signals is not possible. That is the reason why, in the cited document coded signals are only used in high depth areas. Moreover, as the length of coded signals is limited by this propagation duration, the energy that can be carried by a coded signal is limited and consequently, the closer is the area to be imaged, the less the SNR can be improved by using coded signals.

SUMMARY OF THE INVENTION

It is an object of the present invention to propose an improved ultrasound imaging system in order to overcome the above-mentioned problem relating to the apparatus described in the cited document. This ultrasound imaging system uses coded signals to enhance the SNR at any depth of the area to be imaged.

An ultrasound imaging system according to the invention is claimed in claim 1.

In the ultrasound imaging system of the invention, the transmitting group transmits an elongated coded signal while the receiving group allows reception of the reflected signal at the same time by angular reflection. The overlap of the transmission and reception duration no longer imposes a limitation on the length of the coded signal used.

In a preferred embodiment of the invention, a first and a distinct second transducer arrays constitute the first and the distinct second groups of transducer elements.

In an advantageous embodiment of the invention, the probe comprises means for ultrasonic insulation to insulate the two distinct groups of transducer elements. Effectively, as the transmitted signal is stronger than the reflected signal, a part of the transmitted signal could be received by the receiving transducer elements masking the reflected signal.

In a preferred embodiment of the invention the nature of coded signals provided by the transmission means is a sequence whose cyclic autocorrelation is a delta function. The convolution of a delta function with the reflector finction of the tissue is the reflector function itself. For instance, M-sequences constitute coded signals that result, after a cyclic autocorrelation, in a short, sidelobe-free powerful peak. According to the present invention M-sequences used are chosen to have a duration longer than the longest propagation period.

In an advantageous embodiment of the invention the nature of the coded signal provided by the transmission means is a "doubled" or "tripled" sequence whose cyclic autocorrelation is a delta function. This is realized by a signal doubler that outputs a code of double or triple length. This "doubled" or "tripled" signal is transmitted to the probe.

A particular embodiment of the invention comprises correlation means to correlate beam-summed received signals with said coded signals so as to form decoded signals. The correlation of a coded signal which is a "doubled" or "tripled" signal with the M-sequence itself results in a pseudo-cyclic autocorrelation. The substitution of the cyclic autocorrelation by a non-cyclic correlation of the signal with a "doubled" or "tripled" version of said signal offers good results since one half of the resultant signal is then the same as the resultant signal obtained by using the full cyclic autocorrelation. So, doubled M-sequences are used to receive the favorable result of a cyclic convolution in a non-cyclic case.

BRIEF DESCRIPTION OF THE DRAWINGS

The invention is described hereafter in detail in reference to the diagrammatic figures wherein.

DESCRIPTION OF EMBODIMENTS

The present invention relates to an ultrasound imaging system for imaging ultrasound scatterers in a medium.

Figure 1:
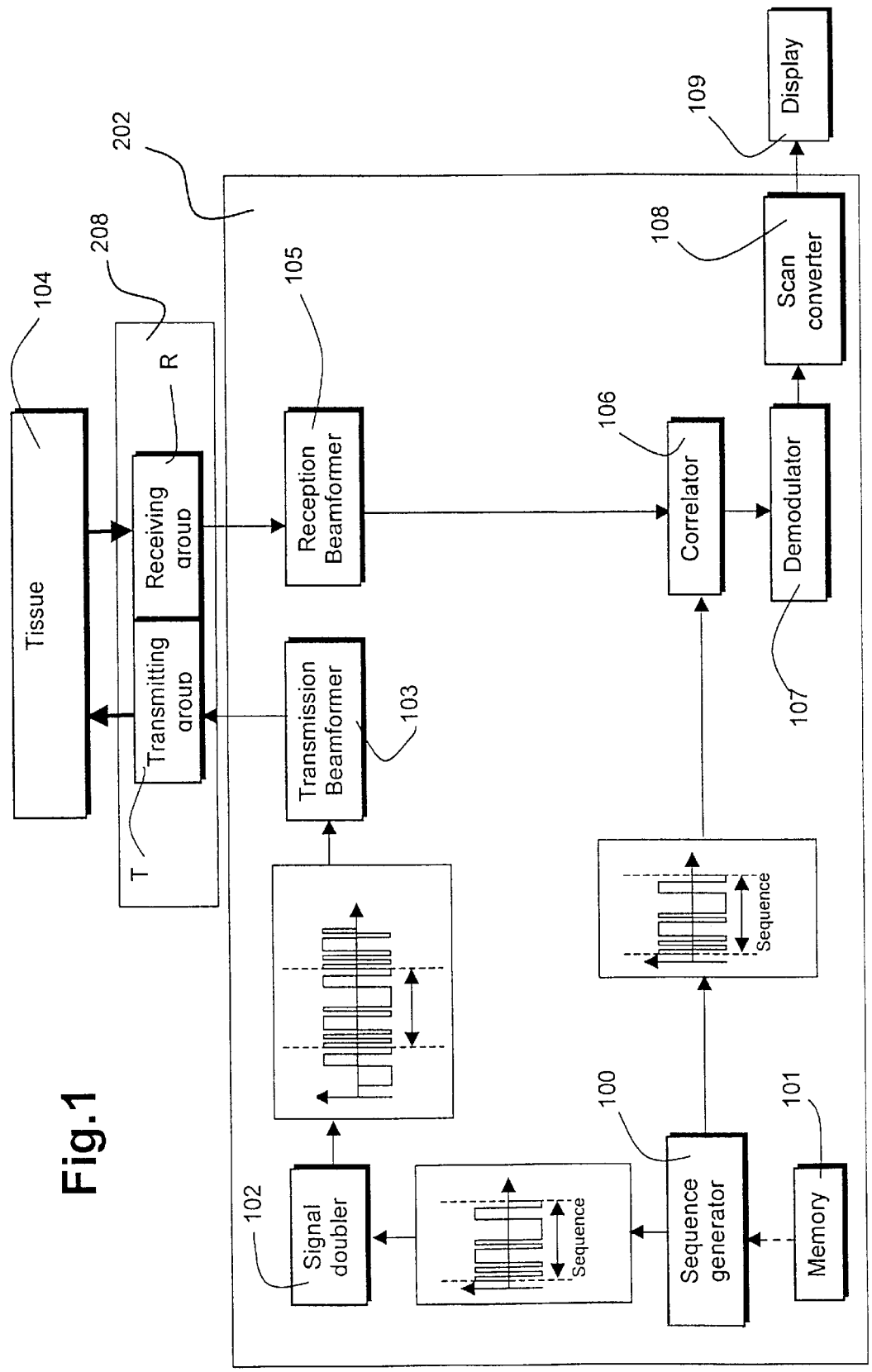
FIG. 1 shows a block diagram of an ultrasound system for imaging scatterers in a medium.

Referring to FIG. 1, this ultrasound imaging system comprises a probe 203 that comprises two distinct groups of transducer elements: a first group labeled transmitting group T to transmit ultrasound waves and a second group labeled receiving group R for detecting ultrasound echoes reflected by said ultrasound scatterers. In an embodiment of the invention, these two distinct groups can exchange their functions: the original transmitting group serving as receiving group while the original receiving group is serving as transmitting group. In one embodiment, the first and second distinct groups of transducer elements are formed by two distinct transducer arrays. In a particular embodiment, the transmitting group and the receiving group can be each one group of transducer elements belonging to a single transducer. In this case, the two distinct groups of transducer elements could not be spatially separated but mixed as, for instance, an alternation of one transmitting element, one receiving element, one transmitting element . . . These mixed groups can be configurable in order that the transmitting or the receiving function is selected separately for each element, allowing various modifications in characteristics of the excitation of a tissue 104.

A processing system 202 controls the configuration of the two distinct groups of transducer elements if needed, provide ultrasound signal to the probe 203 and process ultrasound data from the probe 203.

An elongated coded signal is transmitted by the transmitting group T of transducer elements to a tissue 104 and echoes reflected by ultrasound scatterers present in the tissue 104 are received by the receiving group R at the same time by angular reflection. Therefore the overlap of the transmission and reception duration does not imply anymore a limitation on the length of the used coded signal. In these embodiments, coded signals of arbitrary length can be used, which leads to a theoretically unlimited increase of SNR, only restricted by the aspired frame rate. As the image quality of ultrasonic images is determined by the mean frequency and the bandwidth of the ultrasonic signal, this SNR improvement can be traded in for increased resolution by using coded signals with a higher mean frequency and bandwidth. So, even in frequency ranges where there is strong signal attenuation, the SNR can be improved by using coded signals.

In this embodiment, a sequence generator 100 outputs a sequence of the signal or fetches said signal from a memory 101. Suitable sequences are, for example chirp sequences, maximum sequences or Barker/Golay etc. codes. The amplitude of the signal does not exceed the voltage corresponding to the maximum allowed peak pressure of ultrasound signals in biological tissue.

This is necessary to obtain a sidelobe-free resultant signal after the processing of the received coded signal.

In the cited document U.S. Pat. No. 5,984,869 the sidelobe-free resultant signal is obtained by using two complementary Golay-codes which show complementary sidelobes that are eliminated by addition of the two resultant data streams. This solution absolutely requires an extremely precise alignment of the two received signals; such alignment is uncertain as the patient could move somewhat. Moreover, this solution requires two transmissions: one transmission for each complementary Golay-code. Since it is necessary to wait for the propagation of the first Golay-code before sending the second Golay-code, the duration of a scan is twice the propagation time to the outmost scatterer.

Instead, a preferred embodiment of the system of the invention comprises a sequence generator 100 for generating a sequence, whose cyclic autocorrelation is a delta function. The convolution of a delta function with the reflector function of the tissue is the reflector function itself. For instance, M-sequences constitute coded signals that result, after a cyclic autocorrelation, in a short, sidelobe-free powerful peak. In the present invention, M-sequences used are chosen to have a duration longer than the longest propagation period.

Since the signal resulting from the echoes reflected by the scatterers is the result of the convolution of the M-sequence with the scatterer function, it has a length different from the length of the sequence itself and cannot be correlated cyclically with it. As a matter of fact, the transmission of a cyclic M-sequence by repeating it over and over, ends up with ambiguities concerning the scatterer positions. If instead just one M-sequence is transmitted to avoid problems implied by a cyclic repetition of M-sequences, multiple copies of this transmitted sequence are obtained, added together after the convolution with the scatterer function. In this case the correlation of the received signal with the original M-sequence has unacceptable sidelobes.

The solution to these problems is to use a pseudo-cyclic correlation which allows a processing result to be obtained that is totally free of sidelobes. The M-sequence is "doubled" in the signal doubler 102 to allow a pseudo-cyclic correlation of the reflected "doubled" M-sequence with the original M-sequence. The aim is to ensure that the "good, cyclic, sidelobe-free" half of the resultant signal of the correlation of the M-sequence with the "doubled" M-sequence is in one block and in a known place. To have the good part of the resultant signal located in the central part of the resultant signal, the later half of the sequence is attached to the beginning of a whole M-sequence and the front half of the sequence is attached to the back of the signal. In another embodiment, the sequence is "tripled" using, a signal "tripler", so as to realize a pseudo-cyclic correlation. The resultant "doubled" (or "tripled") signal is a high-energy signal with a long duration compared to conventional signals. This signal is transmitted to a transmission beamformer 103 that can be a part of a single beamformer which also includes a reception beamformer 105.

In the transmission beamformer 103, for each of the transmitting transducer elements of the transmitting transducer T, comprising for example 128 elements in the proposed embodiment, the "doubled" signal is delayed according to the distance between the transducer elements of the transmitting transducer T and a focus point, just as it is done in the apparatus described in the cited document. Each focusing operation determines a propagation focusing line from the transmitting transducer T to the focus point.

Figure 2:
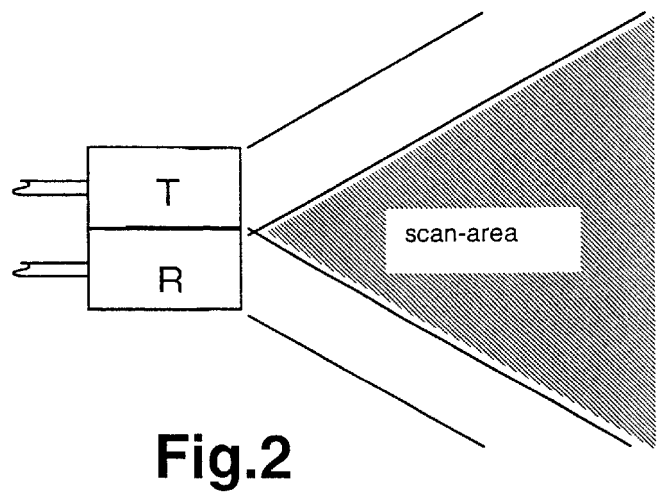
FIG. 2 shows an arrangement of two groups of transducer elements and the corresponding scanning area.
Figure 3:
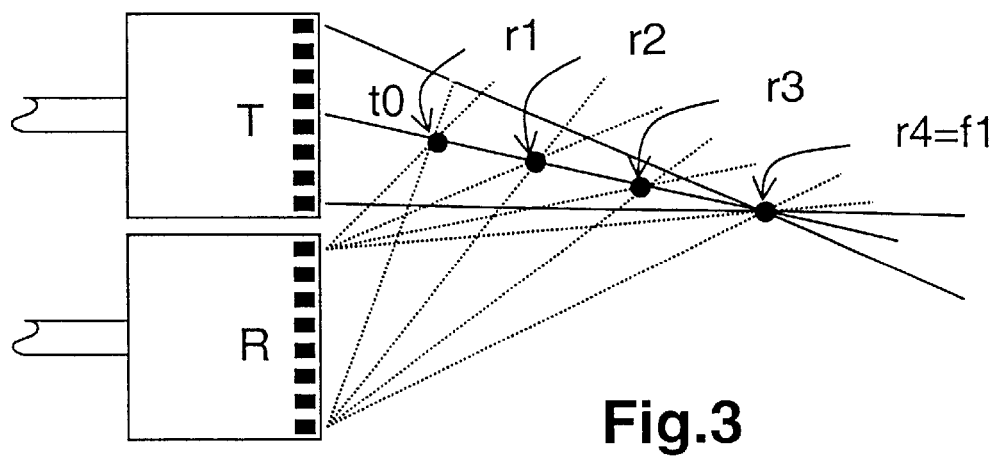
FIG. 3 illustrates the functioning of the transmission and reception focusing.

Referring to FIG. 3, illustrating the electronic beamforming in the case of an arrangement of two transducers in the same plane as presented in FIG. 2, the transducer elements of the transmitting transducer T are stimulated with the elongated signal in such a way that constructive interference of the ultrasonic signal occurs at a focus point f1 and, to a lesser extent, along a line starting at a point t0 on the transducer surface and intersecting the focus point f1, said line being labeled propagation focusing line.

After transmission of the signal in parallel by the transducer elements of the transmitting transducer T so as to stimulate the tissue 104, a focused ultrasonic signal propagates through the tissue 104 and is reflected at impedance discontinuities and travels back to the receiving transducer R. At each transducer element of the receiving transducer R the received ultrasonic signals are recorded and transmitted to a reception modified delay-and-sum beam-former 105 which can be a part of a single beam-former used for transmitted and received signals.

Figure 4:
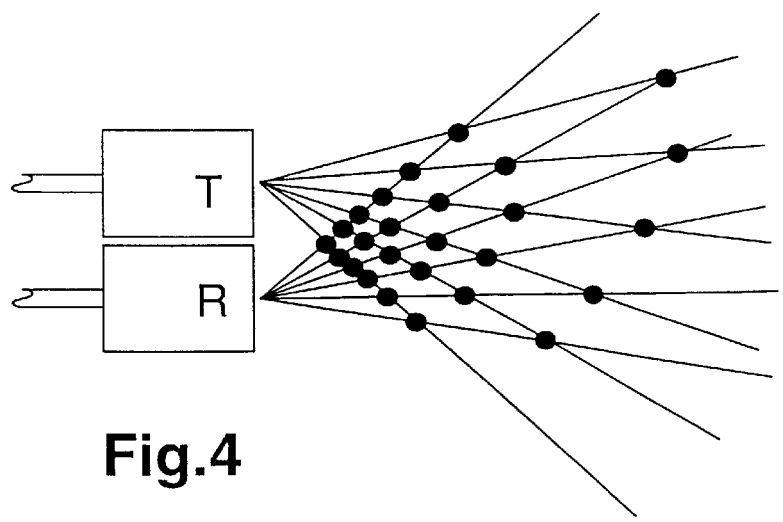
FIG. 4 illustrates the result of the sampling of the scanning area.

Referring to FIG. 3 the role of the reception modified delay-and-sum beam-former 105 is to focus the received data to a number of reception focus points that are positioned on the propagation focusing line that has no intersection with the receiving transducer: a set of reception focus delays is calculated according to the differences of the distances from the various points to the receiving transducer elements by the reception beam-former 105 for a certain number of focus points (r1, r2, r3, r4 . . . ) on the propagation focusing line (t0, f1). This dynamic focusing requires additional computational resources, since reception beam-forming has to be performed for every point of the image. FIG. 4 illustrates the result available after such reception beam-forming: a densely sampled imaging plane located on beams that start at the transmitting transducer.

Signals obtained from the reception beamformer 105 are correlated with the original sequence, being is the non-doubled version, in a correlator 106. All distortions caused by the influence of this pseudo-cyclic correlation are situated at the ends of the resultant data stream. These ends are cut off. So, after correlation of the received signals with the original M-sequence, a line of data shows the result of cyclic correlation of an M-sequence correlated with the scatterer function and allows the determination of the scatterers' strengths and positions. After demodulation in a demodulator 107, data are transferred to a scan converter 108 that rearranges the A-scans, being a discrete sampling of the object, in an appropriate order (fan-like, rectangle, diamond-shape . . . ) to allow the display of an image by a display device 109.

FIG. 2 illustrates an arrangement of two groups of transducer elements in a common plane. The regions that can be insonified by the two transducers overlap partially: this region of overlap defines the scan-area. In this arrangement, for low depth imaging, strong crosstalk, which results in a masking of the received signal by the transmitted signal, is likely to occure between neighboring transducer elements from the two groups of transducer elements since the transmitted signal is stronger than the received reflected signal. According to an advantageous embodiment of the invention, the probe comprises means for ultrasonic insulation to avoid the effects of the transmitted signal on receiving transducer elements. Ultrasonic insulation means between the transmitting group and the receiving group can be implemented in the above-mentioned embodiments by using a sound-absorbing layer of ultrasonic insulating material between the transmitting transducer elements and the receiving transducer elements, by determining a special spatial arrangement, for example, by setting back the receiving group of transducer elements relatively to the transmitting group of transducer elements, or by combinations of such measures. In another feasible embodiment, means for insulation to avoid the influence of the perfectly known transmitted signal on the received signal consist in subtracting, by analog hardware or by digital processing implemented in the processing system 202, the transmitted signal that is caused directly by transmitting elements on the receiving elements.

Figure 5:
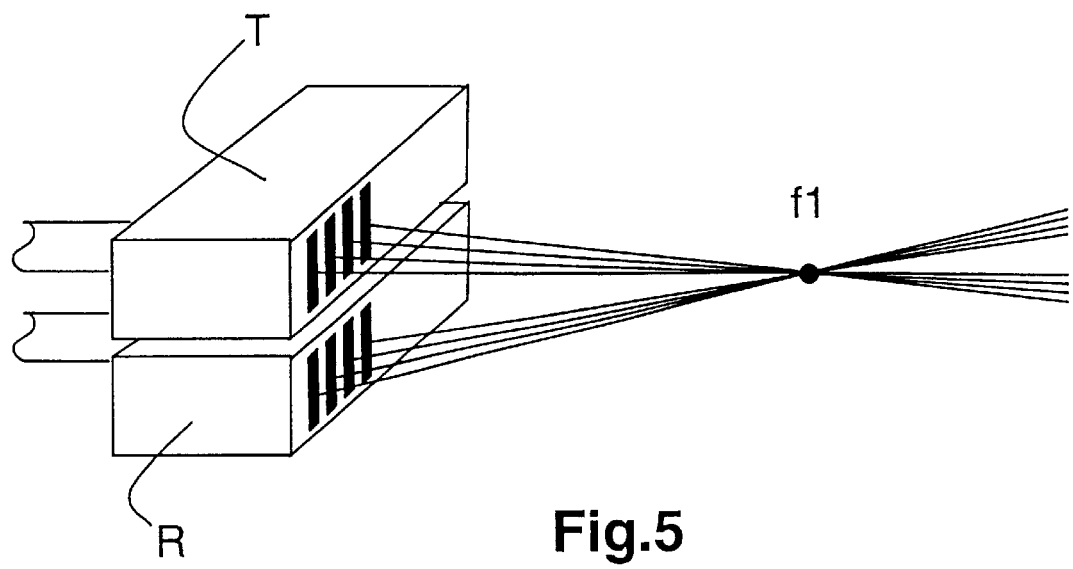
FIG. 5 shows another example of an arrangement of an ultrasound system comprising two transducers.

FIG. 5 illustrates another arrangement for a probe comprising two transducers, a transmitting transducer T and a receiving transducer R, positioned in different planes. An alignment of the two groups of transducer elements in parallel provides good ultrasonic insulation and allows optimum focusing on focus point f1 belonging to the scan-area that is supported by a plane parallel to the planes carrying the two transducers and situated between these two planes.

In implementations of the invention as presented in FIG. 2 and FIG. 3, the two transducers can be fixed in a common plane or in different planes by a mounting arrangement or by a common housing. Decoupled groups of transducer elements of one transducer array can also be used. The transducers used can be any kind of combination of phased-arrays, linear-arrays, curved-arrays or other transducer models. The two distinct groups of transducer elements can especially be implemented as subapertures of a two-dimensional ultrasonic transducer array. The two groups of transducer elements can be arranged on flat surfaces like on two linear or phased arrays or can be arranged on curved surfaces like on two curved arrays or on combinations thereof. These groups can be controlled as usually for linear arrays (parallel beams) or phased arrays (fan beams) or combinations thereof.

Figure 6:
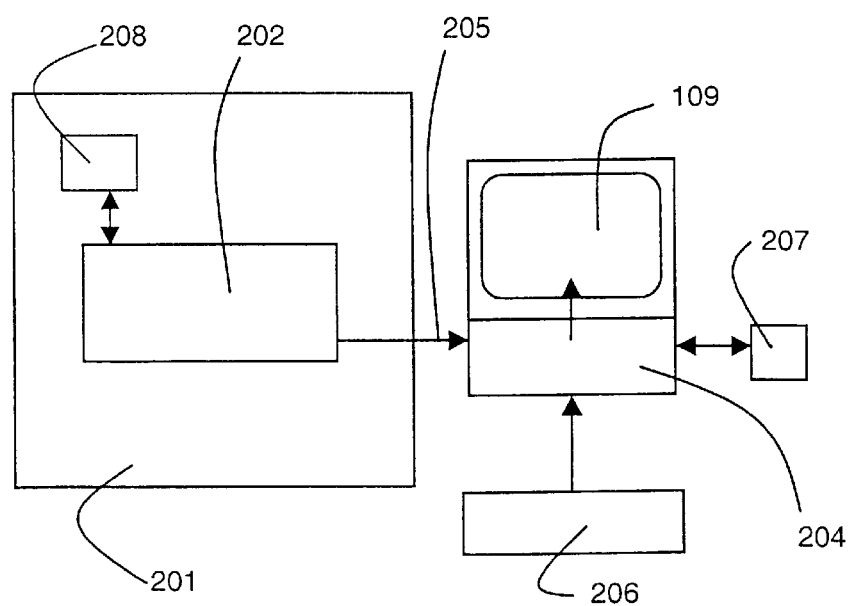
FIG. 6 illustrates the implementation of the invention in a medical ultrasound examination imaging apparatus.

Referring to FIG. 6, a medical ultrasound examination imaging apparatus 201 comprises means for imaging ultrasound scatterers. This apparatus comprises a processing system 202 for processing ultrasound data as above described. The medical ultrasound examination apparatus comprises a probe 203 to acquire ultrasound data and means for providing this ultrasound data to the processing system 202 which has at least one output 205 to provide image data to display and/or storage means 109, 204. The display and storage means may be the screen 109 and the memory, respectively, of a workstation 204. Said storage means may alternatively be external storage means. This image processing system 202 may be a suitably programmed computer of the workstation 204, or a special purpose processor having circuit means, such as LUTs, memories, filters, logic operators, that are arranged to perform the functions and calculations according to the invention. The workstation 204 may also comprise a keyboard 206 and a mouse 207.

What is claimed is:

1. An ultrasound imaging system for imaging ultrasound scatterers, said ultrasound image system comprising:
 a probe for transmitting ultrasound waves and detecting ultrasound echoes reflected by said ultrasound scatterers, wherein said probe includes a first group of transducer elements, labeled transmitting group, to transmit ultrasound waves and a distinct second group of transducer elements, labeled receiving group, to detect ultrasound echoes reflected by the ultrasound scatterers;
 transmission and reception means, coupled to said probe, for providing coded signals to said transmitting group and for receiving signals from said receiving group respectively;
 transmission beam-forming means for focusing the ultrasound waves on a focus line;
 reception beam-forming means for forming beam-summed received signals from signals received from the focus line;
 processing means for processing the beam-summed received signals so as to form decoded signals; and
 means for displaying an image that is a function of the decoded signals.

2. The system of claim 1, wherein a first transducer array and a distinct second transducer array constitute the first group of transducer elements and the distinct second group of transducer elements.

3. The system of one of the claim 1, wherein the probe further includes means for ultrasonic so as insulation to insulate the two distinct groups of transducer elements.

4. The system of one of the claim 1, wherein coded signals provided by the transmission means are based on a sequence whose cyclic autocorrelation function is a delta function.

5. The system of claim 4, wherein the type of coded signals provided by the transmission means is a "doubled" or "tripled" sequence whose cyclic autocorrelation function is a delta function.

6. The system of claim 1, wherein said processing means includes correlation means to correlate beam-summed received signals with said coded signals so as to form said decoded signals.

7. The system of claim 1, further comprising:

a suitably programmed computer or a special purpose processor having circuit means which are arranged to process ultrasound data.

8. An ultrasound diagnostic imaging apparatus having a system with a probe as claimed in claim 7 for acquiring and processing medical ultrasound data, and also having display means for displaying medical digital images and processed medical digital images.

9. Method of processing signals and data of the system as claimed in claim 1, comprising the steps of:

providing coded signals to said transmitting group of transducer elements;

receiving signals from said receiving group of transducer elements;

focusing ultrasound waves on a focus line by beamforming;

forming beam-summed received signals from signals received from the focus line;

processing the beam-summed received signals so as to form decoded signals; and displaying an image which is a function of the decoded signals.

10. A computer program product comprising a set of instructions for carrying out a method of processing signals and data of the system as claimed in one of claim 1.

* * * * *